US009408731B2

(12) United States Patent
Hartley et al.

(10) Patent No.: US 9,408,731 B2
(45) Date of Patent: Aug. 9, 2016

(54) METHOD AND DEVICE FOR TREATING AORTIC DISSECTION

(75) Inventors: David Ernest Hartley, Subiaco (AU); Ian Nixon, Victoria (AU); Peter John Mossop, Victoria (AU)

(73) Assignee: Cook Medical Technologies LLC, Bloomington, IN (US)

( * ) Notice: Subject to any disclaimer, the term of this patent is extended or adjusted under 35 U.S.C. 154(b) by 2483 days.

(21) Appl. No.: 10/726,963

(22) Filed: Dec. 3, 2003

(65) Prior Publication Data

US 2004/0176832 A1   Sep. 9, 2004

Related U.S. Application Data

(60) Provisional application No. 60/430,825, filed on Dec. 4, 2002.

(51) Int. Cl.
| | | |
|---|---|---|
| *A61F 2/89* | (2013.01) | |
| *A61F 2/90* | (2013.01) | |
| *A61F 2/07* | (2013.01) | |
| A61F 2/82 | (2013.01) | |
| A61F 2/848 | (2013.01) | |

(52) U.S. Cl.
CPC ... *A61F 2/90* (2013.01); *A61F 2/07* (2013.01); *A61F 2/89* (2013.01); *A61F 2002/826* (2013.01); *A61F 2002/828* (2013.01); *A61F 2002/8483* (2013.01); *A61F 2002/8486* (2013.01); *A61F 2220/0016* (2013.01); *A61F 2220/0075* (2013.01)

(58) Field of Classification Search
USPC .............. 623/1.11, 1.13, 1.16, 1.12, 1.23
See application file for complete search history.

(56) References Cited

U.S. PATENT DOCUMENTS

| 4,902,508 A | | 2/1990 | Badylak et al. | |
|---|---|---|---|---|
| 5,387,235 A | | 2/1995 | Chuter | |
| 5,571,170 A | * | 11/1996 | Palmaz et al. | 623/1.11 |
| 5,662,700 A | * | 9/1997 | Lazarus | 606/194 |
| 5,711,969 A | | 1/1998 | Patel et al. | |
| 5,720,776 A | | 2/1998 | Chuter et al. | |
| 5,733,337 A | | 3/1998 | Carr, Jr. et al. | |
| 5,769,887 A | * | 6/1998 | Brown et al. | 623/1.23 |
| 5,797,949 A | | 8/1998 | Parodi | |

(Continued)

FOREIGN PATENT DOCUMENTS

| WO | WO98/22158 | 5/1998 |
|---|---|---|
| WO | WO98/53761 | 12/1998 |

(Continued)

OTHER PUBLICATIONS

U.S. Appl. No. 60/392,667, Hartley et al., filed Jun. 28, 2002.

(Continued)

*Primary Examiner* — Ryan J Severson
(74) *Attorney, Agent, or Firm* — Brinks Gilson & Lione

(57) ABSTRACT

A prosthesis adapted for inter-luminal placement by endovascular deployment for the treatment of vascular dissection, the prosthesis has a self expanding stents (38) connected together to define an elongate lumen wall engaging surface. At least one of the stents has a bio-compatible graft material cover (36) to define a covered portion (25). The cover is adapted to close off a rupture (7) in the wall of the lumen (6) and the stents are adapted to provided pressure on the wall of the lumen adjacent to and extending away from the rupture.

4 Claims, 5 Drawing Sheets

(56) References Cited

U.S. PATENT DOCUMENTS

| | | | |
|---|---|---|---|
| 5,824,040 A * | 10/1998 | Cox et al. | 623/1.35 |
| 5,855,619 A | 1/1999 | Caplan et al. | |
| 5,955,110 A | 9/1999 | Patel et al. | |
| 5,968,096 A | 10/1999 | Whitson et al. | |
| 6,004,347 A * | 12/1999 | McNamara et al. | 623/23.64 |
| 6,221,096 B1 * | 4/2001 | Aiba et al. | 623/1.11 |
| 6,287,271 B1 | 9/2001 | Dubrul et al. | |
| 6,309,412 B1 * | 10/2001 | Lau et al. | 623/1.11 |
| 6,355,056 B1 | 3/2002 | Pinheiro | |
| 6,383,214 B1 | 5/2002 | Banas et al. | |
| 6,508,782 B1 * | 1/2003 | Evans et al. | 604/22 |
| 6,939,370 B2 | 9/2005 | Hartley et al. | |
| 7,238,198 B2 | 7/2007 | Hartley et al. | |
| 2001/0037142 A1 * | 11/2001 | Stelter et al. | 623/1.13 |
| 2001/0041928 A1 * | 11/2001 | Pavcnik et al. | 623/1.13 |
| 2002/0049453 A1 * | 4/2002 | Nobles et al. | 606/139 |
| 2002/0058985 A1 * | 5/2002 | DePalma et al. | 623/1.13 |
| 2002/0058986 A1 * | 5/2002 | Landau et al. | 623/1.13 |
| 2002/0120327 A1 * | 8/2002 | Cox et al. | 623/1.16 |
| 2002/0147492 A1 | 10/2002 | Shokoohi et al. | |
| 2002/0198587 A1 * | 12/2002 | Greenberg et al. | 623/1.13 |
| 2003/0204245 A1 * | 10/2003 | Brightbill | 623/1.16 |
| 2004/0054396 A1 | 3/2004 | Hartley et al. | |
| 2004/0073289 A1 | 4/2004 | Hartley | |
| 2004/0098079 A1 | 5/2004 | Hartley et al. | |

FOREIGN PATENT DOCUMENTS

| | | |
|---|---|---|
| WO | WO99/29262 | 6/1999 |
| WO | WO00/09041 | 2/2000 |
| WO | WO00/42947 | 7/2000 |
| WO | WO03/053287 | 7/2003 |

OTHER PUBLICATIONS

U.S. Appl. No. 60/391,737, Hartley et al., filed Jun. 26, 2002.
International Search Report PCT/US03/38388, EPO, Oct. 14, 2004.
Written Opinion PCT/US03/38388, EPO, Oct. 14, 2004.

* cited by examiner

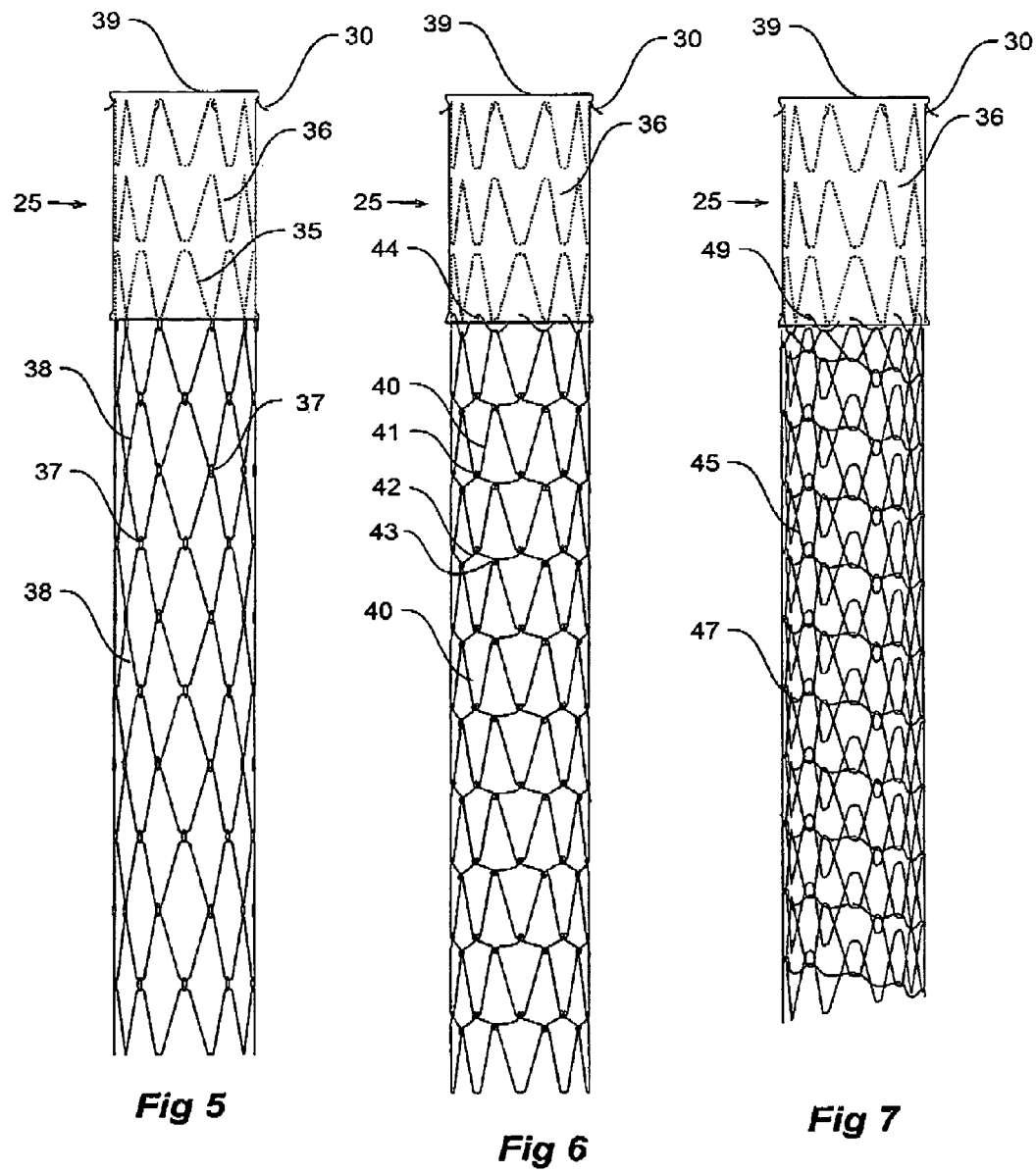

METHOD AND DEVICE FOR TREATING AORTIC DISSECTION

CROSS-REFERENCE TO RELATED APPLICATIONS

This application claims priority of provisional application Ser. No. 60/430,825, filed Dec. 4, 2002.

TECHNICAL FIELD

This invention relates to a method and a device for the treatment of aortic arch disease and more particularly to the treatment of a form of aortic aneurysm known as an aortic dissection.

BACKGROUND OF THE INVENTION

An aortic dissection is a form of aneurysm to the descending aorta in which the wall of the aorta is damaged to such an extent that blood under pressure can get between inner and outer layers of the wall of the aorta to expand part of the wall into an inflated sac of blood which is referred to as a false lumen. The inflated sac of blood or false lumen so formed may extend some distance down the descending aorta and open out into the aorta again further down.

It is the object of this invention to provide a device and a method of treatment of such an aortic dissection.

Throughout this specification the term proximal with respect to both human or animal vasculature and the deployment device and prosthesis will be used to refer to the region closest to the heart or that part of the deployment device or of the prosthesis which when in use is closest to the heart and the term distal will be used for regions of the human or animal vasculature further from the heart and those parts of the deployment device or prosthesis which in use are further from the heart.

SUMMARY OF THE INVENTION

In one form therefore the invention is said to reside in a prosthesis adapted for inter-luminal placement by endovascular deployment, the prosthesis comprising a plurality of self expanding stents together defining an elongate substantially cylindrical lumen wall engaging surface and at least one of the stents having a bio-compatible graft material cover whereby the cover is adapted to close off a rupture in the wall of the lumen and the stents are adapted to provide pressure on the wall of the lumen adjacent to and extending away from the rupture.

Preferably the cover portion encompasses two or three stents and the cover is stitched or otherwise fastened to the stents in the covered portion.

Preferably the covered portion of the prosthesis is at the proximal end of the plurality of stents.

The uncovered other stents preferably extend away from the covered portion and may be linked by suitable flexible links. Alternatively the uncovered stents may be linked by a thread or fibre such as a suture threaded through the bends of the zig-zag stents. The thread or fibre such as a suture may be connected to each bend by a knot such as for example, a half hitch, a thumb knot, two half hitches, a clove hitch or a similar knot.

The proximal end of the covered portion of the prosthesis may include barbs extending from the stents through the cover to engage with the wall of the lumen when deployed.

In one preferred embodiment of the invention there may be three covered stents each of the zig-zag type and constructed from stainless steel or nitinol and up to eight or ten uncovered stents formed from stainless steel or nitinol.

The uncovered stents may be of the Gianturco type zigzag stent and constructed so that in their expanded state they provide a low but useful radial force on the aorta wall.

Alternatively the uncovered portion may be in the form of a self expanding spiral of zig-zag configuration.

In a further form the invention may be said to reside in a prosthesis for treatment of an aortic dissection comprising a substantially cylindrical body in the expanded state having at least one self expanding stent covered by a bio-compatible graft material and a self expanding stent assembly extending from a distal end thereof.

There may be included barbs extending from the proximal end of the graft.

In one embodiment the self expanding stent assembly extending from a distal end of the biocompatible graft material may be formed from a biocompatible and biodegradable mesh material so that after it has performed its work of providing a radial pressure onto the wall of the aorta it can biodegrade in the bloodstream.

The stents in these embodiments of the invention may be made MRI (Magnetic Resonance Imaging) compatible.

In one form the stent may be in the form of a Gianturco style zig zag Z stent. Alternatively the stent may be a Nitinol™ self expanding stent of the type known as a Zilver™ stent sold by Cook Incorporated.

The bio-compatible graft material may be either on the inside or the outside of the covered portion of the prosthesis.

In a further form the invention may be said to reside in a deployment device and prosthesis for treatment of an aortic dissection, the prosthesis comprising a substantially cylindrical body in the expanded state having at least one self expanding stent covered by a bio-compatible graft material and a self expanding stent assembly extending from a distal end thereof, and the deployment device comprising an elongate catheter adapted to be deployed over a guide wire, a nose cone at the proximal end of the elongate catheter, a trigger wire arrangement adapted to retain a proximal end of the prosthesis in a retracted state, a sheath arrangement over the elongate catheter adapted to retain the prosthesis in a contracted state around the elongate catheter, means at the distal end of the elongate catheter to release the trigger wire arrangement and means to withdraw the sheath arrangement.

Preferably the elongate catheter includes means to supply an angiographic contrast medium at a distal end thereof through the catheter and the nose cone includes discharge ports for the angiographic contrast medium.

In an alternative form the invention is said to reside in a method of treatment of aortic dissection disease comprising the steps of loading a prosthesis onto a deployment device, the prosthesis comprising a plurality of self expanding stents together defining an elongate substantially cylindrical lumen wall engaging surface and at least one of the stents having a bio-compatible graft material cover whereby the cover is adapted to close off a rupture in the wall of the lumen, the deployment device including means to retain the proximal end of the prosthesis in a retracted state and a trigger wire arrangement to release the proximal end of the prosthesis, a sheath to retain the entire prosthesis in a retracted state and means to withdraw the sheath, endovascularly deploying the deployment device with the prosthesis loaded thereon to the site of the aortic dissection, checking by radiographic techniques that the covered stent or stents are at the site of the aortic dissection, withdrawing the sheath to expose the covered stent or stents of the prosthesis, releasing the proximal end of the prosthesis by means of releasing the trigger wire arrangement, withdrawing the sheath to deploy the other stents of the prosthesis along the wall of the lumen such that they provide pressure against the wall of the lumen, and withdrawing the deployment device.

Preferably the covered stent or stents are at the proximal end of the prosthesis.

The bio-compatible material may be dacron, expanded polytetrafluoroethylene or other synthetic bio-compatible material.

While Dacron, expanded polytetrafluoroethylene (ePTFE), or other synthetic biocompatible materials can be used to fabricate the coverings for the stent graft and the tubular extension, a naturally occurring biomaterial, such as collagen, is highly desirable, particularly a specially derived collagen material known as an extracellular matrix (ECM), such as small intestinal submucosa (SIS). Besides SIS, examples of ECM's include pericardium, stomach submucosa, liver basement membrane, urinary bladder submucosa, tissue mucosa, and dura mater.

SIS is particularly useful, and can be made in the fashion described in Badylak et al., U.S. Pat. No. 4,902,508; Intestinal Collagen Layer described in U.S. Pat. No. 5,733,337 to Carr and in 17 Nature Biotechnology 1083 (November 1999); Cook et al., WIPO Publication WO 98/22158, dated 28 May 1998, which is the published application of PCT/US97/14855. Irrespective of the origin of the material (synthetic versus naturally occurring), the material can be made thicker by making multilaminate constructs, for example SIS constructs as described in U.S. Pat. Nos. 5,968,096; 5,955,110; 5,885,619; and 5,711,969. Animal data show that the SIS used in grafts can be replaced by native tissue in as little as a month's time. In addition to xenogenic biomaterials, such as SIS, autologous tissue can be harvested as well. Additionally Elastin or Elastin-Like Polypetides (ELPs) and the like offer potential as a material to fabricate the graft to form a device with exceptional biocompatibility. Another alternative would be to use allographs such as harvested native tissue. Such tissue is commercially available in a cryopreserved state.

U.S. Pat. No. 5,387,235 entitled "Endovascular Transluminal Prosthesis For Repair Of Aneurysms" discloses apparatus and methods of retaining grafts onto deployment devices. These features and other features disclosed in U.S. Pat. No. 5,387,235 could be used with the present invention and the disclosure of U.S. Pat. No. 5,387,235 is herewith incorporated in its entirety into this specification.

U.S. Pat. No. 5,720,776 entitled "Stent Barb" discloses improved barbs with various forms of mechanical attachment to a stent. These features and other features disclosed in U.S. Pat. No. 5,720,776 could be used with the present invention and the disclosure of U.S. Pat. No. 5,720,776 is herewith incorporated in its entirety into this specification.

PCT Patent Publication No. WO98/53761 entitled "A Prosthesis and a Method of Deploying a Prosthesis" discloses an introducer for a prosthesis which retains the prosthesis so that each end can be moved independently. These features and other features disclosed in PCT Patent Publication No. WO98/53761 could be used with the present invention and the disclosure of PCT Patent Publication No. WO98/53761 is herewith incorporated in its entirety into this specification.

U.S. Provisional Patent Application No. 60/392,667, now Ser. No. 10/609,846 filed Jun. 30, 2003, and PCT Patent Application No. PCT/US03/204963 filed Jun. 30, 2003, entitled "Thoracic Deployment Device" discloses introducer devices adapted for deployment of stent grafts particularly in the thoracic arch. This feature and other features disclosed in U.S. Provisional Patent Application No. 60/392,667 could be used with the present invention and the disclosure of U.S. Provisional Patent Application No. 60/392,667 is herewith incorporated in its entirety into this specification.

U.S. Provisional Patent Application No. 60/391,737, now Ser. No. 10/602,930, filed Jun. 24, 2003, and PCT Patent Application No. PCT/US03/19997, filed Jun. 24, 2003, entitled "Stent-Graft Fastening Arrangement" discloses arrangements for fastening stents onto grafts particularly for exposed stents. This feature and other features disclosed in U.S. Provisional Patent Application No. 60/391,737 could be used with the present invention and the disclosure of U.S. Provisional Patent Application No. 60/391,737 is herewith incorporated in its entirety into this specification.

U.S. Utility patent application Ser. No. 10/647,642 entitled "Asymmetric Stent Graft Attachment" discloses retention arrangements for retaining onto and releasing prostheses from introducer devices. This feature and other features disclosed in U.S. Utility patent application Ser. No. 10/647,642 could be used with the present invention and the disclosure of U.S. Utility patent application Ser. No. 10/647,642 is herewith incorporated in its entirety into this specification.

PCT Patent Publication No. WO03/053287 entitled "Improving Graft Adhesion" discloses arrangements on stent grafts for enhancing the adhesion of such stent grafts into walls of vessels in which they are deployed. This feature and other features disclosed in PCT Patent Publication No. WO03/053287 could be used with the present invention and the disclosure of PCT Patent Publication No. WO03/053287 is herewith incorporated in its entirety into this specification.

BRIEF DESCRIPTION OF THE DRAWING

This then generally describes the invention but to assist with understanding reference will now be made to the drawings which show a preferred embodiment of the invention. In the drawings:

FIG. 5 shows a prosthesis according to one embodiment of this invention;

FIG. 6 shows an alternative embodiment of the prosthesis according to the invention; and FIG. 7 shows a still further embodiment of the prosthesis according to the invention.

DETAILED DESCRIPTION

Figure 1:
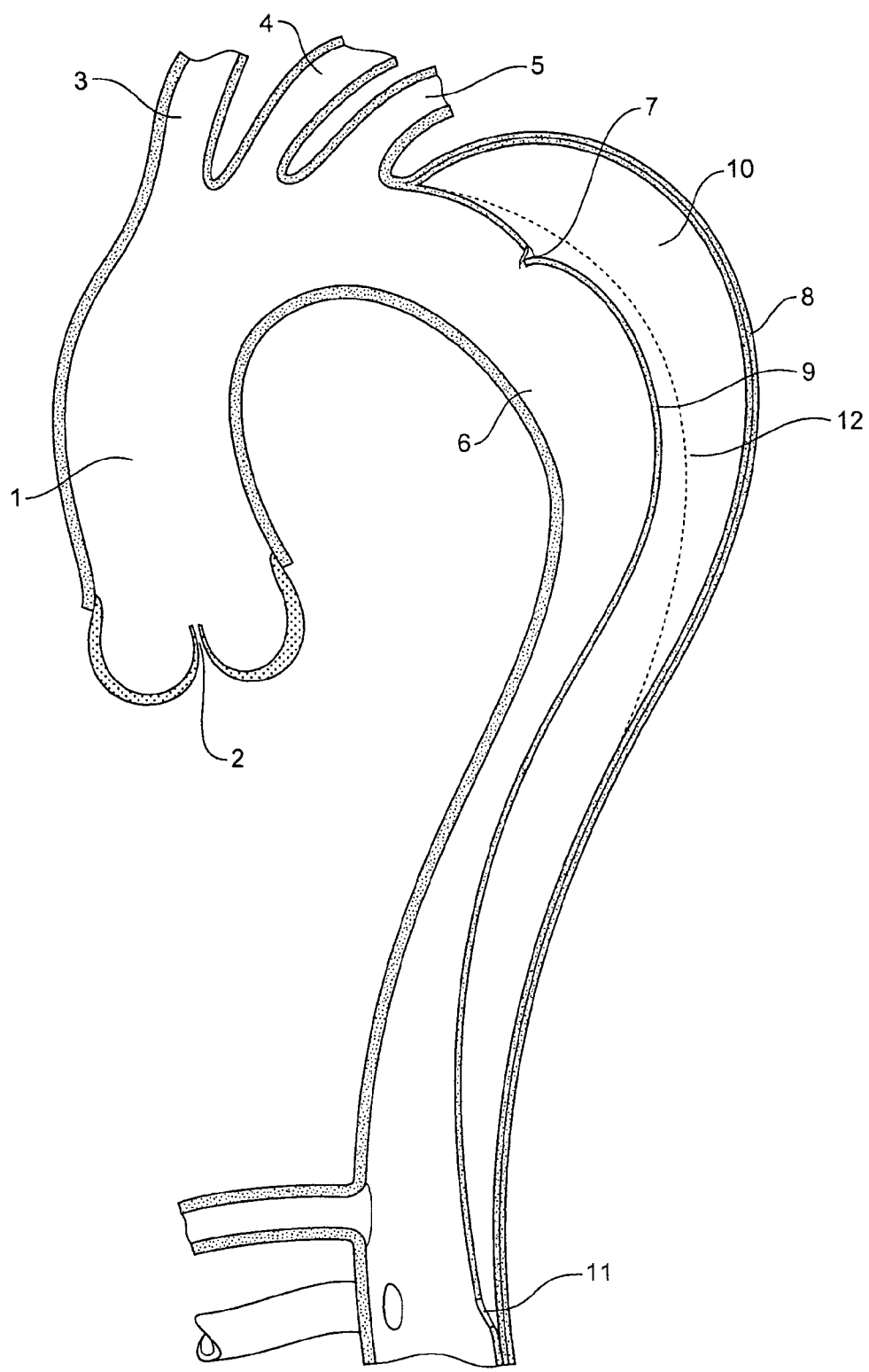
FIG. 1 shows a schematic view of an aorta with an aortic dissection.

Looking more closely to the drawings and in particular FIG. 1 it will be seen that the aorta comprises an ascending aorta 1 which receives blood from the heart though an aortic valve 2. At the upper end of the ascending aorta there are branches for the innominate artery 3 the left common carotid artery 4 and the subclavian artery 5. The aorta after these is referred to as the descending aorta 6 and it is in this region that an aortic dissection can occur. In an aortic dissection the wall of the descending aorta can be injured such as by a traumatic injury so that a partial rupture or tear 7 occurs and the wall of the descending aorta splits so that there is an outer wall 8 and an inner wall 9 between which a false lumen 10 occurs. At some distance down the false lumen 10 the false lumen may again open out into the aorta 6 such as at 11. The dotted line 12 shows the normal position of the wall of the aorta.

Treatment of the aortic dissection requires that the rupture 7 be closed off and the false lumen deflated.

Figure 2:
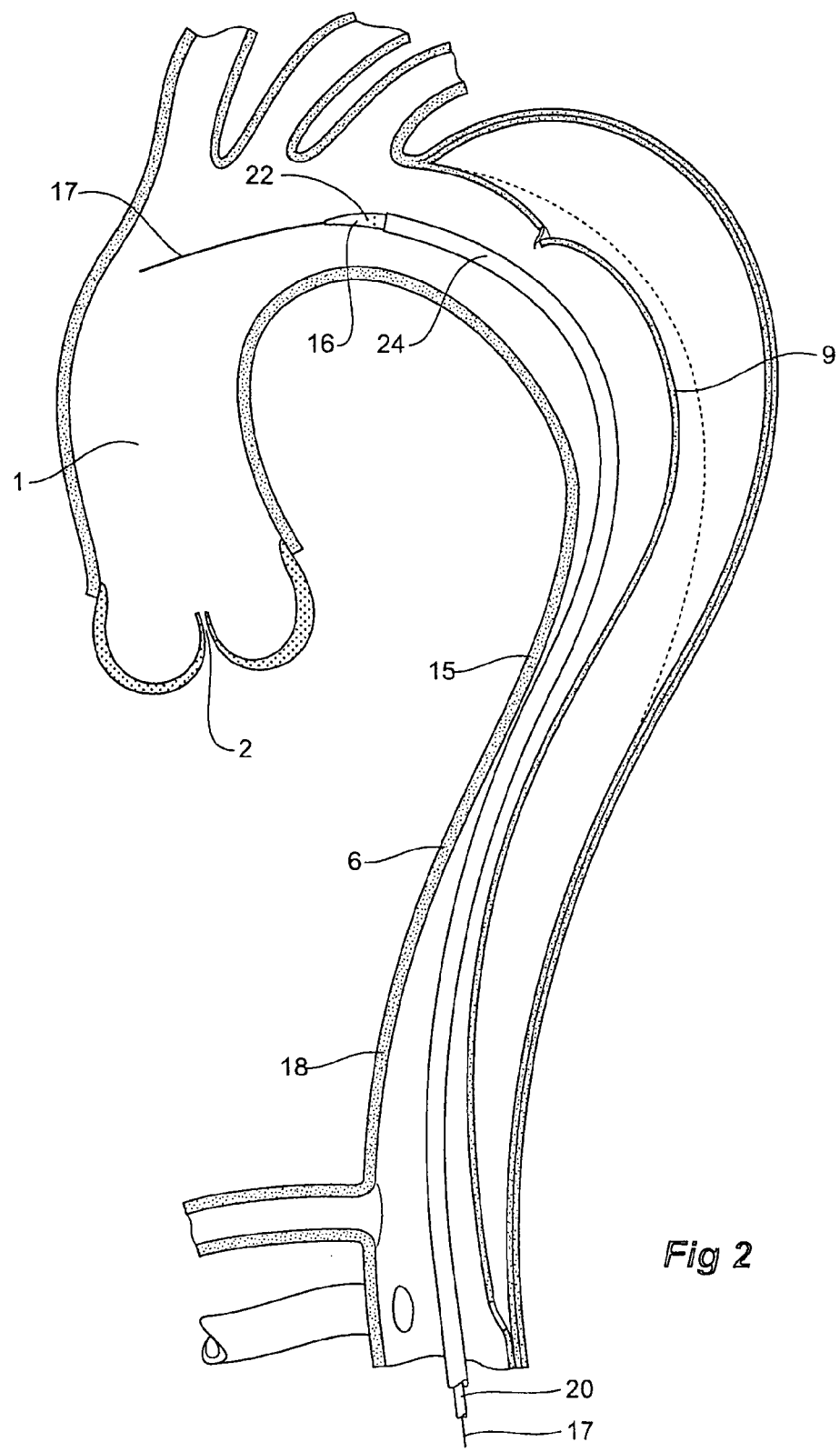
FIG. 2 shows the aorta shown in FIG. 1 with a deployment device inserted therein.

As can be seen in FIG. 2 a deployment device 15 with a nose cone 16 has been advanced over a guide wire 17 through the true lumen 18 of the descending aorta 6. Preferably the deployment device is inserted through a femoral artery and up through the iliac arteries into the aorta.

Once the deployment device is in substantially the correct place angiographic fluids may be supplied through a hollow elongate catheter 20 in the deployment device to exit through apertures 22 in the nose cone so that with the angiographic contrast medium the region can be visualised by radiographic techniques.

Figure 3:
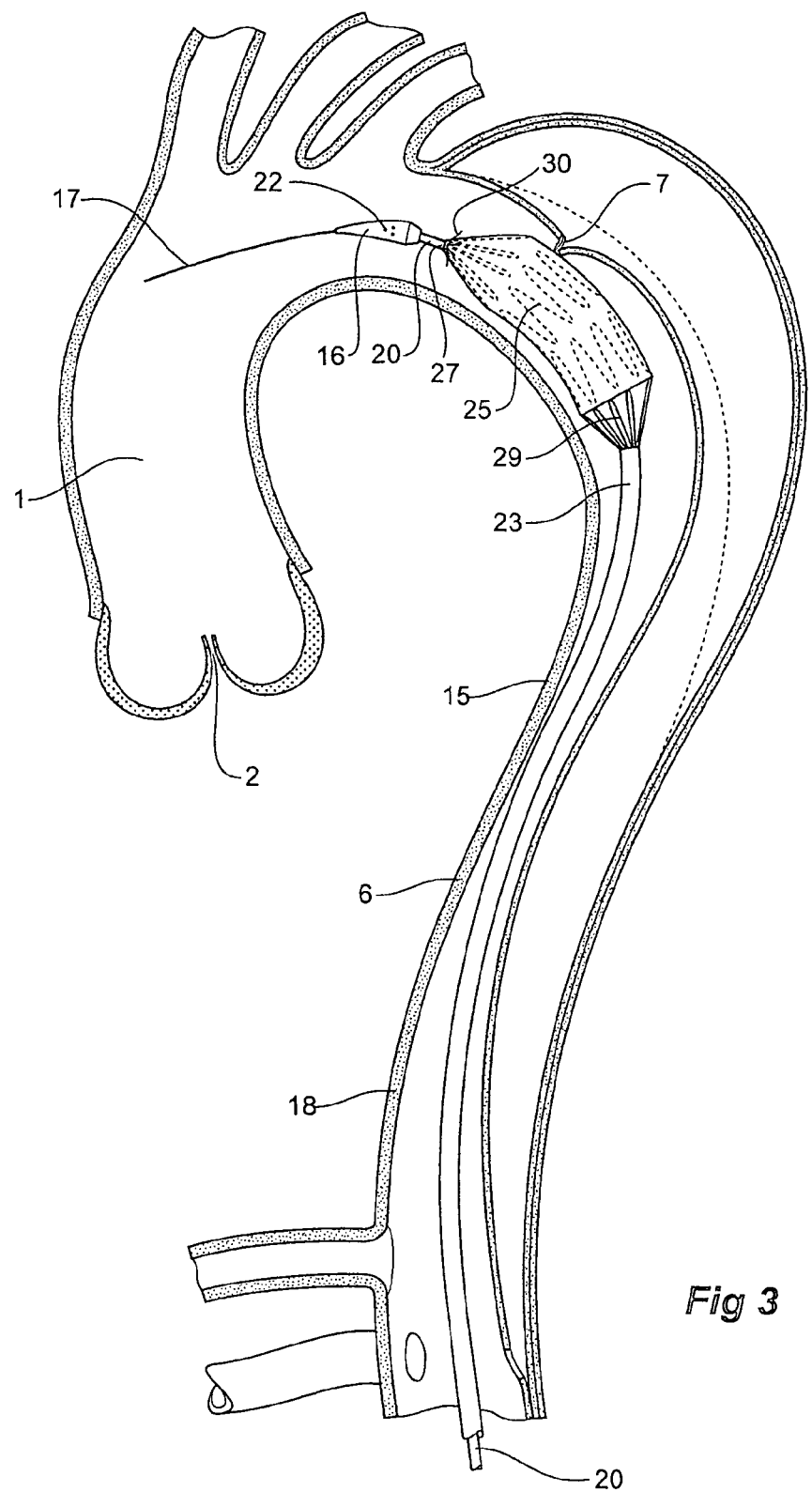
FIG. 3 shows the first stage of deployment of the prosthesis.

When the deployment device is found to be in the correct position the sheath 24 of the deployment device is withdrawn to the position as shown in FIG. 3 at which stage the covered portion 25 of the prosthesis is exposed except that the proximal end 27 is retained by a trigger wire mechanism to the central catheter 20. The sheath is withdrawn until the first of the uncovered stents 29 of the prosthesis are exposed. At this stage the pressure of blood flow from the heart will still tend to cause blood flow around the prosthesis.

Figure 4:
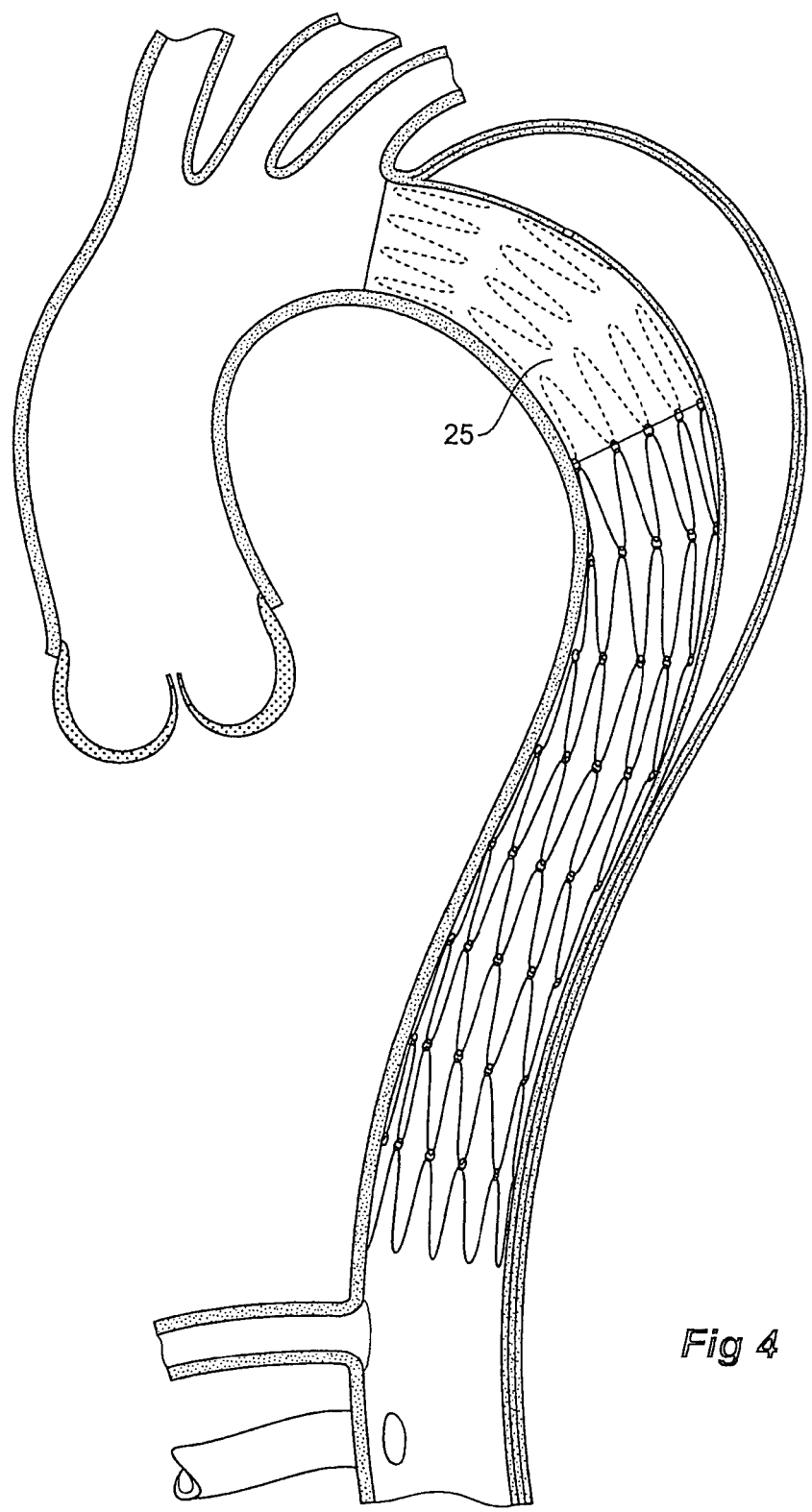
FIG. 4 shows the fully deployed prosthesis.

Next the trigger wire mechanism is released so that the proximal end 27 of the prosthesis 25 is allowed to open as shown in FIG. 4 and the barbs 30 on the proximal end of 27 of the prosthesis engage against the wall of the aorta to securely fix the covered portion 25 of the prosthesis in the upper end of the descending aorta with the covered portion 25 of the prosthesis covering the rupture 7 and essentially closing it off so that blood can no longer flow into the false lumen 10. Blood can then flow through the covered portion of the prosthesis and exit out the end of the covered portion at the first stent 29 and then as the sheath 23 is continued to be withdrawn the remaining self expanding stents are allowed to engage against the wall of the true lumen 18 and provide pressure onto the wall particularly where the false lumen occurs to gradually deflate and close off the false lumen as finally shown in FIG. 4. At this stage the sheath 23 is advanced to the nose cone 16 and the deployment device is withdrawn.

FIG. 5 shows a prosthesis for use with the method of the present invention. The prosthesis has three stents 35 under a biocompatible graft material cover 36 which provides the covered portion 25 of the prosthesis and a number of uncovered stents 38 each of which are linked to the next stent up or down by flexible links 37. The covered portion is joined to the uncovered portion by links. The flexible links enable each stent to expand separately as the false lumen is deflated which may occur over a period of several days or weeks. The stents provide gradual pressure on the wall of the lumen to close the false lumen and open up the true lumen.

It will be realised that different numbers of covered stents and uncovered stents may be used depending upon the nature of the aortic dissection and the length of aorta to be opened and the dimensions of the rupture in the wall of the aorta.

Barbs 30 are provided at the proximal end 39 of the prosthesis.

The stents 35 may be Gianturco zigzag Z stents or any other form of self expanding stent. Alternatively the stents 35 may be balloon expanded stents.

The prosthesis may have a total length of from 100 to 300 mm and a diameter when expanded of 22 to 45 mm. The covered portion may have a length of from 50 to 150 mm and a diameter when expanded of 22 to 45 mm.

As discussed earlier the stents 38 and the links 37 may be in the form of a mesh and formed from a biocompatible and biodegradable mesh material so that after it has performed its work of providing a radial pressure onto the wall of the aorta it can biodegrade in the bloodstream.

FIG. 6 shows a further embodiment of a prosthesis according to the present invention.

In this embodiment the covered portion is the same as in the previous embodiment shown in FIG. 5 but the uncovered self expanding stents 40 are linked by means of a fibre or thread 42 such as a suture so that each self expanding stent can act independently of its neighbours. Where each fibre or suture 42 passes a bend 41 of a stent there may be a knot 43 such as a clove hitch to assist with the controlled linking of adjacent stents. Threads or sutures 44 join the proximal uncovered stents 40 to the covered portion 25 of the prosthesis.

FIG. 7 shows a still further embodiment of the prosthesis of the invention.

In this embodiment the covered portion is the same as in the previous embodiment shown in FIG. 5 but the uncovered portion is formed from a continuous spiral of zig-zag stent 45 with again loops in adjacent spirals joined by a thread 47 such as a suture. Again suitable knots may be used to assist with the controlled linking of adjacent portions of the spiral stent. Threads or sutures 49 join the uncovered spiral stent 45 with the covered portion 25 of the prosthesis.

Throughout this specification various indications have been given as to the scope of the invention but the invention is not limited to any one of these but may reside in two or more of these combined together. The examples are given for illustration only and not for limitation.

What is claimed is:

1. An aortic dissection treatment prosthesis comprising: a proximal covered portion and a distal uncovered portion, the distal uncovered portion being fastened to and extending distally from the proximal covered portion;

the proximal covered portion comprising a tubular body of a biocompatible graft material and at least three self expanding stents within the tubular body and supporting the tubular body to provide an outside sealing surface;

the distal uncovered portion comprising a plurality of self expanding stents linked together by flexible links and defining an elongate substantially cylindrical and flexible lumen wall engaging surface, the flexible links comprising a thread or fiber connected between adjacent stents in the uncovered stent assembly, wherein the stents of the uncovered stent assembly comprise bends and the stents of the uncovered stent assembly are linked to adjacent stents by the thread or fiber between adjacent bends of the stents and wherein there are from eight to ten uncovered stents of the plurality of stents in the uncovered stent assembly each of the stents being of a zig-zag type and being formed from stainless steel or nitinol;

the proximal covered portion providing a cover for an aortic dissection to close off the dissection so that blood can no longer flow therethrough and the distal uncovered portion providing gradual pressure to close a false lumen of the aortic dissection and open up a true lumen with the flexible links between adjacent bends of the stents enabling each stent to expand separately as the false lumen is closed off.

2. A prosthesis as in claim 1 wherein the thread or fiber is connected to each bend by a knot selected from a half hitch, a thumb knot, two half hitches or a clove hitch.

3. A prosthesis as in claim 1 wherein a proximal end of the covered portion of the prosthesis includes barbs extending from a stent of the plurality of stents through the cover to engage with the wall of the lumen when deployed.

4. A prosthesis as in claim 1 wherein the uncovered stent assembly is in the form of a self expanding spiral stent of zig-zag configuration.

\* \* \* \* \*